(12) United States Patent
Derry

(10) Patent No.: US 11,304,640 B2
(45) Date of Patent: Apr. 19, 2022

(54) SENSOR FOR ELECTRODE AND PROCESSES FOR PRODUCTION

(71) Applicant: 3M INNOVATIVE PROPERTIES COMPANY, Saint Paul, MN (US)

(72) Inventor: Cameron E. Derry, London (CA)

(73) Assignee: 3M Innovative Properties Company, St. Paul, MN (US)

( * ) Notice: Subject to any disclaimer, the term of this patent is extended or adjusted under 35 U.S.C. 154(b) by 102 days.

(21) Appl. No.: 16/063,382

(22) PCT Filed: Dec. 5, 2016

(86) PCT No.: PCT/US2016/064920
§ 371 (c)(1),
(2) Date: Jun. 18, 2018

(87) PCT Pub. No.: WO2017/112394
PCT Pub. Date: Jun. 29, 2017

(65) Prior Publication Data
US 2019/0000337 A1 Jan. 3, 2019

Related U.S. Application Data

(60) Provisional application No. 62/270,683, filed on Dec. 22, 2015.

(51) Int. Cl.
*A61B 5/265* (2021.01)
*A61B 5/268* (2021.01)
(Continued)

(52) U.S. Cl.
CPC .............. *A61B 5/276* (2021.01); *A61B 5/259* (2021.01); *A61B 5/265* (2021.01); *A61B 5/268* (2021.01);
(Continued)

(58) Field of Classification Search
CPC ............ A61B 5/0408; A61B 2562/125; A61B 2562/0209; A61B 5/25; A61B 5/259; A61B 5/263; A61B 5/265; A61B 5/268
See application file for complete search history.

(56) References Cited

U.S. PATENT DOCUMENTS 3,834,373 A 9/1974 Sato
3,976,055 A 8/1976 Monter
(Continued)

FOREIGN PATENT DOCUMENTS

CA 2585355 10/2005
CN 203636902 U 6/2014
(Continued)

OTHER PUBLICATIONS

International Search Report for PCT/US2015/064920 dated Mar. 16, 2017.
(Continued)

*Primary Examiner* — Eun Hwa Kim

(57) ABSTRACT

An electrode sensor involves a solid conductive polymeric substrate shaped as an electrode sensor or portion of an electrode sensor having a layer of silver-coated particles distributed on and embedded into a surface of the substrate. The electrode sensor is particularly useful for ECG electrodes and utilizes less silver without unduly sacrificing performance. A process for producing the electrode sensor involves distributing a layer of silver-coated particles on a surface of a solid conductive polymeric substrate shaped as an electrode sensor or portion of an electrode sensor and thermally embedding the silver-coated particles into the surface. The process is simpler and less costly than existing processes for producing electrode sensors.

20 Claims, 2 Drawing Sheets

200 um

(51) Int. Cl.
  *H01B 1/22* (2006.01)
  *A61B 5/276* (2021.01)
  *A61N 1/04* (2006.01)
  *A61B 5/259* (2021.01)

(52) U.S. Cl.
  CPC ........... *A61N 1/046* (2013.01); *A61N 1/0456* (2013.01); *A61N 1/0496* (2013.01); *H01B 1/22* (2013.01); *A61B 2562/0209* (2013.01); *A61B 2562/125* (2013.01)

(56) References Cited

U.S. PATENT DOCUMENTS

| | | | |
|---|---|---|---|
| 4,377,170 | A | 3/1983 | Carim |
| 4,635,642 | A | 1/1987 | Cartmell |
| 4,727,881 | A | 3/1988 | Craighead |
| 4,848,348 | A | 7/1989 | Craighead |
| 4,938,219 | A | 7/1990 | Ishii |
| 5,331,959 | A * | 7/1994 | Imran .................. A61B 5/0408  252/500 |
| 5,337,748 | A * | 8/1994 | McAdams ............. A61B 5/259  600/396 |
| 5,406,945 | A | 4/1995 | Riazzi |
| 5,489,215 | A | 2/1996 | Wright |
| 5,626,135 | A * | 5/1997 | Sanfilippo ............ A61N 1/0492  600/391 |
| 5,782,761 | A | 7/1998 | Gusakov |
| 6,415,170 | B1 | 7/2002 | Loutis |
| 6,511,701 | B1 | 1/2003 | Divigalpitiya |
| 6,569,494 | B1 | 5/2003 | Chambers |
| 6,650,922 | B2 | 11/2003 | Kurata |
| 6,834,612 | B2 | 12/2004 | Chambers |
| 6,919,504 | B2 | 7/2005 | McCutcheon |
| 7,034,403 | B2 | 4/2006 | Divigalpitiya |
| 8,637,136 | B2 | 1/2014 | Ferguson |
| 9,192,313 | B1 | 11/2015 | Lisy |
| 2005/0261565 | A1 | 11/2005 | Lane |
| 2009/0253975 | A1 | 10/2009 | Tiegs |
| 2010/0159197 | A1 | 6/2010 | Ferguson |
| 2013/0037987 | A1 | 2/2013 | Clarke |
| 2013/0085368 | A1 | 4/2013 | Coggins |
| 2018/0215941 | A1* | 8/2018 | Hagar .................. H01B 1/22 |

FOREIGN PATENT DOCUMENTS

| | | |
|---|---|---|
| CN | 104952551 A | 9/2015 |
| EP | 0195859 | 10/1986 |
| EP | 0597156 | 5/1994 |
| WO | WO 84/02423 | 6/1984 |
| WO | WO 98/02088 | 1/1998 |
| WO | WO 02/089906 | 11/2002 |
| WO | WO 2011/106730 | 9/2011 |
| WO | WO 2013/049467 | 4/2013 |

OTHER PUBLICATIONS

International Search Report for PCT/US2015/063948 dated Mar. 17, 2017.
International Search Report for PCT/US2015/063956 dated Mar. 6, 2017.
"Conductive polymer" from Wikipedia, the free encyclopedia; Dec. 11, 2015; 6 pgs; available at https//web.archive org/web/20151211045601/ https://en.wikipediaorg/wiki/Conductive_polymer (XP055347878).
"Poly(p-phenylene sulfide)" from Wikipedia, the free encyclopedia; May 8, 2015; available at https://web.archive.org/web/20150508022926/ http://en.wikipedia.org/wiki/Polyphenylene_sulfide (XP055347876).
"Ryton—Polyphenyl Sulfide, Polymer Plastics Company, LC, Carson City, Nevada;" Sep. 16, 2015; available at https://web.archive.org/web/20150916115247/http://www.polymerplastics.com/performance_ryton.shtml (XP055347872).

* cited by examiner 100 um 200 um 300 um 500 um

SENSOR FOR ELECTRODE AND PROCESSES FOR PRODUCTION

CROSS REFERENCE TO RELATED APPLICATIONS

This application is a national stage filing under 35 U.S.C. 371 of International Application No. PCT/US2016/064920, filed Dec. 5, 2016, which claims the benefit of U.S. Provisional Application No. 62/270,683, filed Dec. 22, 2015. The disclosures of both applications are incorporated by reference in their entirety herein.

This application relates to medical devices, in particular to medical electrodes.

BACKGROUND

The basic function of a medical electrode is to act as half a galvanic cell to convert ionic potential of the body into an electrical signal, which can be displayed as an output. Silver is commonly used as the metal in this half-cell due to the fact it is non-polarizable. In defibrillation during heart failure, sensors must 'recover' quickly from the accumulated charge and operate normally. The non-polarizing nature of silver, which contributes to this quick recovery time, is why it is used in sensors for ECG electrodes almost exclusively.

Originally, ECG sensors were re-usable and made entirely out of silver. To reduce cost, current electrode sensors comprise a plastic resin, and covered with silver only on the outer surface. Covering the plastic resin with silver is generally accomplished by any one of a number of methods including electroplating, ink printing and silver sputtering.

SUMMARY

There remains a need for sensors, particularly for ECG, in which the overall amount of silver is low while not unduly sacrificing operational performance.

There is provided an electrode sensor comprising: a solid conductive polymeric substrate shaped as an electrode sensor or portion of an electrode sensor; and, a layer of silver-coated particles distributed on and embedded into a surface of the substrate.

There is further provided a process for producing an electrode sensor comprising: distributing a layer of silver-coated particles on a surface of a solid conductive polymeric substrate shaped as an electrode sensor or portion of an electrode sensor; and, thermally embedding the silver-coated particles into the surface.

The sensor is less costly and simpler and quicker to produce without unduly sacrificing performance in comparison to traditional electroplated and printed silver ink sensors.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1A:
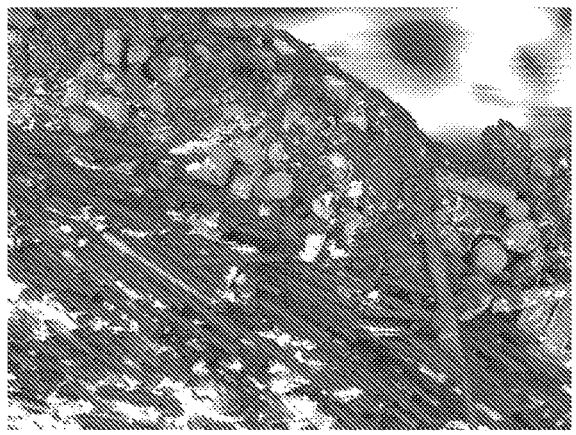
FIG. 1A is a scanning electron micrograph (SEM) image at 400× magnification of an eyelet cross section, cut down the middle, showing silver-coated glass fibers (light gray) embedded in a surface of a substrate comprising a conductive polymeric resin.

The electrode sensor comprises a layer of silver-coated particles distributed on and embedded into a surface of the substrate. The silver-coated particles may function in an ionic transducer component in the electrode. It is desirable that only the surface of the substrate to be in contact with a subject's skin or a conductive gel or adhesive on the subject's skin (i.e. a contact surface) has silver coated thereon and embedded therein because only the contact surface requires silver to be present in order for the sensor to function in the desired fashion, for example to provide quick recovery of the sensor after accumulating excess charge, during a defibrillation event. Sensors herein may be conveniently manufactured to provide such features, reducing the overall amount of silver required to manufacture the sensor. However, if desired, other surfaces of the substrate may also comprise silver-coated particles distributed thereon and embedded therein.

Because a bulk of the silver-coated particles are made of a non-silver component, much of the silvered layer of the substrate is occupied by the non-silver component, in contrast to ink printed and electroplated silver layers where the entirety of the layer is occupied by silver. Due to this, the silver particle layer needs a higher total volume, and therefore more individual particles, than a silver ink layer. Thus, the present sensor possesses much higher surface area for a given silver amount than in ink printed or electroplated sensors. In the present sensor, the surface area of silver present in the layer may be controlled by controlling shape and size of the silver-coated particles used to create the layer on the substrate. The amount of silver present in the layer can be controlled by controlling the total weight of particles added and their respective silver concentrations. The ability to control the amount of silver further permits the use of less silver overall and less silver per unit area or per unit volume at the surface of the substrate. Such control also permits balancing the amount of silver at the surface with desired performance characteristics of the sensor to reduce production costs of the sensor without sacrificing the desired performance. The sensor has better efficiency of response for the same overall amount of silver.

The amount of silver may be controlled so that silver is present in the layer in an amount of about 10 mg Ag/sq. in. (4.65 g/m$^2$) or less, or even 8 mg Ag/sq. in., or even 6 mg Ag/sq. in., or even 3 mg Ag/sq. in., in relation to the surface area of the layer. In some embodiments, the amount of silver may be controlled so that the silver is present in the layer in an amount in a range of about 1-10 mg Ag/sq. in., or 1-8 mg Ag/sq. in., or 1-6 mg Ag/sq. in., or 1-3 mg Ag/sq. in. The amount of silver in electroplated sensors of the prior art is typically over about 10 mg Ag/sq. in. The amount of silver may be controlled to provide the sensor with a pre-determined recovery time from charge accumulated by the sensor, for example in a defibrillation event during heart failure. Because the silver-coated particles are on and embedded in the surface, the bulk of the sensor does not comprise silver. Therefore, silver is not dispersed in the bulk of the substrate, the silver only being present at the surface, or at the surface and up to a certain relatively small depth in the surface. Further, silver-coated particles are distributed non-continuously on the surface of the substrate providing a plurality of conductive channels, rather than a single conductive channel as provided by the continuous layer of silver resulting from ink printing or electroplating processes. Preferably, surface roughness, as measured by the arithmetic average ($R_a$) of the absolute values of the vertical deviations of the roughness profile from the mean line, is in a range of about 1-15 micron, more preferably about 5-10 micron, for example in a range of about 6.5-7.5 micron.

Simulated defibrillation recovery (SDR) as per AAMI EC12:2000 test method TS-667 may be used to determine recovery performance. In accordance with this test method, recovery potential of the sensors is desirably under 100 mV after 5 seconds from the 4th defibrillation. Sensors of the present invention may have a simulated defibrillation recovery of 100 mV or less, or even 25 mV or less, thereby fulfilling accepted recovery performance criteria for ECG electrodes.

Some types of electrodes require the silvered component to be pre-chlorinated in order to function, for example in order to interact with different gels. In such applications, the silver coating the particles may be partially pre-chlorinated to provide a mixture of silver (Ag) and silver chloride (AgCl) in the layer. Chlorination of the silver may be accomplished by any suitable method, for example by contacting the silver with a chlorinating agent. Chlorinating agents include, for example, chlorine-containing anions such as chlorite ($ClO_2^-$), chloride ($Cl^-$), etc., in the presence of an oxidizing agent for silver if required. Counter cations for the chlorine-containing anions may include, for example, alkali metals (e.g. $Li^+$, $Na^+$, $K^+$, etc.) The silver may be chlorinated to provide a desired ratio of silver to silver chloride provided there is sufficient silver remaining for the desired function and performance. The ratio of silver coated particles to silver chloride coated particles is preferably in a range of about 25:75 to 50:50.

The silver-coated particles may be of any suitable composition, shape and size. For example, the particles may comprise glass, plastic resin (e.g. thermoset or thermoplastic resins), quartz, or the like. The particles may be solid or hollow. The particles may be substantially spherical (e.g. beads), flakes, fibers, or the like. Fibers are of particular note. The particles preferably have an average size of about 500 μm or less, more preferably in a range of about 1-300 μm, more preferably in a range of about 2-200 μm. Substantially spherical particles preferably have an average particle diameter in a range of about 4-100 μm. Flakes and fibers preferably have a longest dimension in a range of about 50-200 μm, more preferably in a range of about 75-150 μm. The size of the particles useable in the present process is in contrast to the size of silver particles in effective ink printing and electroplating processes. Ink printing and electroplating processes typically involve nanometer-sized silver particles, whereas the particle sizes in the present invention may be and preferably are micron-sized. Even the use of micron-sized particles herein provides a much higher surface area for a given silver amount than in ink printed or electroplated sensors using nanometer-sized silver particles. The particles preferably comprise about 1-50 wt % silver based on total weight of the particles, more preferably about 2-40 wt %, more preferably about 4-30 wt %. Mixtures of particles having different compositions, shapes and/or sizes may be used to further control performance properties of the electrode.

The substrate may comprise any polymeric material suitable for use in electrodes. The polymeric material may comprise a thermoplastic resin, a thermoset resin, an elastomeric resin, copolymers thereof or any blend or mixture thereof. The polymeric material preferably comprises a thermoplastic or elastomeric resin. Some particular examples include polyolefin (e.g. polypropylene, such as low density polypropylene (LDPP) or low density polyethylene (LDPE)), polyacrylate, polyethylene terephthalate (PET), acrylonitrile-butadiene-styrene (ABS), poly(dimethylsiloxane) (PDMS), ethylene propylene diene monomer (EPDM) resin, polystyrene and polymeric adhesives (e.g. rubber-based adhesives, acrylic adhesives, etc.).

The polymeric material may comprise usual additives in the polymer industry. Because the substrate does not comprise silver-coated particles dispersed through the bulk of the substrate material, it may be desirable to confer electrical conductivity on the bulk of the polymeric material by using electrically conductive polymers and/or by dispersing one or more electrically conductive fillers in the polymeric material. Some examples of electrically conductive polymers include doped or inherently conductive polyolefins, polythiophenes, polypyrroles, polyanilines and the like. Some examples of electrically conductive fillers include metals (e.g. nickel, iron, and the like) and conductive carbonaceous material (e.g. carbon fiber, carbon black, graphite, polyacrylonitrile (PAN) or particles of the inherently conductive polymers listed above). The electrically conductive filler may be in the form of substantially spherical, flakes, fibers or any mixture thereof.

The particles may be distributed onto the surface of the substrate in any suitable manner provided the density of distributed particles is sufficiently homogeneous on the surface and sufficient to provide enough silver for operation of the electrode. One example includes agitating a hopper full of particles to produce an evenly distributed coating on the substrate, as described in U.S. Pat. No. 6,569,494 issued May 27, 2003, herein incorporated by reference in its entirety. The process of U.S. Pat. No. 6,569,494 includes holding the particles in a hopper having a dispensing opening covered by a screen which has uniformly sized openings that are sufficiently large to allow the largest particles to pass through, yet sufficiently small to hold the particles back when the dispenser is not operating. A cylindrical brush covered with regularly spaced bristles and positioned such that the bristles protrude through openings in the screen is rotated outside the hopper to draw particles through the screen to dispense them onto the surface. The dispensing rate of the particles may be varied by at least one of (a) varying the rotation speed of the brush, (b) adjusting the distance from the screen to the central longitudinal axis of the brush, (c) adjusting the screen opening size, (d) adjusting the brush-to-screen pressure, or (e) adjusting the tension of the screen. Other examples include sifting or electrostatic coating of particles on the substrate. Solvent-less methods of distributing the particles on the surface are preferred.

Once the particles are distributed, they may be thermally embedded into the surface of the substrate. Thermal embedding may involve physically embedding the particles into the surface of the substrate by applying heat and pressure. Embedding the particles into the substrate may be accomplished by any suitable method, for example compression pressing or calendering, using a compression press or calender rolls, for example. Pressure may be applied at a temperature above the softening point (e.g. glass transition temperature ($T_g$)) of the substrate, but preferably less than the melting temperature ($T_m$) of the substrate. The amount of pressure used is preferably controlled so that the particles are only partially embedded, where some silver-coated particles are exposed for interaction with a conductive gel or adhesive while being sufficiently anchored to resist dislodging. In resting electrode applications, the particles preferably provide sufficient density to be percolating. Thus, as a result of physically embedding the particles into the substrate, the particles are well anchored while remaining at the surface. In this way, only the desired surface is provided with silver. The bulk of the substrate and any surfaces not requiring silver remain silver-free; therefore, the overall amount of silver required is reduced and surfaces may be selectively silvered, unlike an electroplating processes. Further, thermally embedding silver-coated particles into the substrate is desirable over silver ink printing, which requires an extensive printing set-up in addition to high temperature drying conditions that limits the type of substrate that can be used. Physically embedding silver-coated particles does not require drying ovens, does not restrict the type of substrate and shortens the production line. Furthermore, thermally embedding dry silver-coated particles into the substrate results in a more environmentally friendly process by avoiding the use of solvents and binders prevalent in ink printing and by avoiding the use of solvents and other highly toxic chemicals prevalent in electroplating.

The electrode sensor may be assembled into an electrode together with other electrode components. The electrode sensor is particularly useful in the fabrication of medical electrodes. Medical electrodes comprise, for example, electrodes for electrocardiography (ECG), electroencephalography (EEG), electromyography (EMG) and transcutaneous electrical nerve stimulation (TENS). An especially preferred electrode for which the sensor is useful is an electrocardiogram (ECG) electrode.

Electrodes comprise the sensor and one or more other components including, for example, a conductive gel or adhesive, a backing, one or more studs and a cover. As described above, the sensor comprises a contact surface through which electrical signals are received from the subject's skin. To enhance electrical contact between the subject's skin and the contact surface of the sensor, the electrode may further comprise a conductive gel or adhesive that act as a conformable conductive interface between the sensor and the subject's skin. In the case of a conductive adhesive, the adhesive also helps secure the electrode to the skin. Where a gel or adhesive is used, the electrode may comprise a removable cover and/or a scrim to protect and contain the gel or adhesive before use. The cover may be removed to expose the gel or adhesive just before use. The electrode may further comprise a backing on a side of the sensor away from the layer of silver-coated particles. The backing may provide support for the substrate and/or a convenient place to handle the electrode without damaging the sensor and/or gel or adhesive. The backing may comprise any suitably handleable material. Polymeric foam backings are preferred as they have a good combination of structural strength for handling, flexibility for conforming the electrode to the subject's skin and low density for reducing overall weight. The sensor may comprise one or more posts that act as lead terminals to which electrical leads may be attached, the electrical leads carrying electrical signal back to an output device. Electrical signals from the subject's skin are conducted through the silver-coated layer (or the conductive gel or adhesive and then the silver-coated layer) though the bulk of the substrate, which comprises electrically conductive polymer or filler, through the one or more posts into the leads and thence to the output device. In some cases, one or more electrically conductive studs (e.g. made of brass, stainless steel or the like) may cover the one or more posts as a way of attaching the backing to the sensor.

The electrode arrangement is not particularly limited and the sensor may be used in any of a wide variety of electrode arrangements in which a silver-coated surface is applicable, for example monitoring ECG electrodes, resting (tab) ECG electrodes and the like. In one embodiment, the electrode arrangement is a resting electrode comprising a flat substrate film with a coating of silver and an ionically conductive adhesive square. Conventional resting electrodes mainly comprise silver inks printed onto the back of a PET film with an ionically conductive adhesive square coated over the silver ink. One embodiment of a resting electrode of the present invention comprises only a layer of silver-coated glass fibers as the conductive layer embedded into an LDPE film with the ionically conductive adhesive square coated over the layer of silver-coated glass fibers. In another embodiment, the electrode arrangement is a monitoring electrode comprising an eyelet having a post and a flange, where the contact surface into which the silver-coated particles are embedded is a face of the flange opposite a face from which the post extends.

EXAMPLES

Materials and Methods:

Three types of silver-coated glass particles were used in the examples—fibers, beads, and flakes. Silver-coated glass particles were used as is from a commercially available source (Potters Industries, Malvern, Pa.). The different samples had different total weight of silver: 12 wt % for beads (S4000-S3), 20 wt % for fibers (SF82TF20), and 30 wt % for flakes (SG35F30).

The fibers, flakes and beads were distributed onto the substrate by similar methods. For example, in accordance with the method described in U.S. Pat. No. 6,569,494 issued May 27, 2003, a hopper full of fibers was agitated to produce an evenly distributed coating on the substrate. Once the particles were distributed, they were physically embedded into the surface of the substrate by applying heat and pressure to produce a silver-coated substrate, which was further used in ECG electrode assembly. Physically embedding the particles into the substrate was accomplished with a compression press or calender rolls. In both cases, the pressure was applied at a temperature that was above the softening point of the substrate material.

Example 1

Figure 1B:
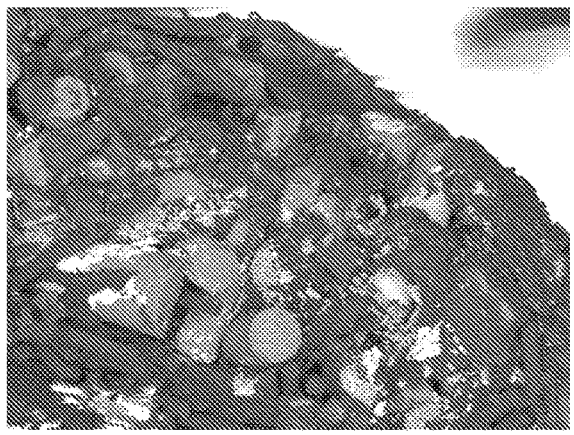
FIG. 1B is the same scanning electron micrograph (SEM) image of FIG. 1A, at 800× magnification.
Figure 1C:
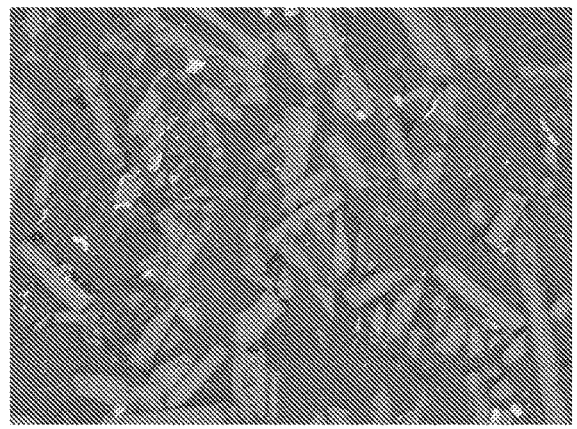
FIG. 1C is a scanning electron micrograph (SEM) image at 400× magnification of the top face an electrode eyelet showing silver-coated glass fibers (light gray) embedded in a surface of a substrate comprising a conductive polymeric resin.
Figure 1D:
FIG. 1D is another scanning electron micrograph (SEM) image at 600× magnification of the top face an electrode eyelet showing silver-coated glass fibers (light gray) embedded in a surface of a substrate comprising a conductive polymeric resin.

Silver-coated glass particles were used to produce sensors for a traditional monitoring ECG electrode. A web of sensor posts protruding from one side was used as the substrate. The sensor web was made of a polypropylene-based conductive resin comprising conductive carbon fibers. Silver-coated glass particles were dispersed onto the flat face of this web, and embedded using a heated compression press at 180° C. under 500 psi for 5 seconds (SEM micrographs of embedded fiber in FIG. 1). The coated web was removed from the press and cooled quickly to room temperature. Sensors were die-cut from the coated web and used to create ECG electrodes. UV-curable electrode gel was applied to the top of the sensor and cured as required. The gel contained salts to convert the silver to silver/silver chloride as described in U.S. Pat. No. 4,377,170 published Mar. 22, 1983. The electrodes were compared to a reference electrode assembled in the same manner with a commercially available sensor (S-9129/300/SP/0.065/AG, available from Select Engineering, Fitchburg, Mass.). Table 1 summarizes the electrical performance of electrodes assembled with Ag-coated particles on sensors. Testing was performed as per AAMI EC12:2000 method TS-667. Desired performance limits are: DC Offset (DCO)=100 mV, AC Impedance (ACZ)=3000 Ohm, Simulated Defibrillation Recovery (SDR)=100 mV.

TABLE 1

| Sample | Ag Fibers | Ag Beads | Ag Flakes | Reference |
| --- | --- | --- | --- | --- |
| Silver Type | 20 wt % Ag coated glass | 12 wt % Ag coated glass | 30 wt % Ag coated glass | Electroplated part |
| Sensor | 40% C fiber in resin | 40% C fiber in resin | 40% C fiber in resin | 20% C fiber in resin |
| DCO (mV) | 0.7 | 0.7 | 0.9 | 0.6 |
| ACZ (Ohm) | 450 | 308 | 223 | 100 |
| SDR (mV) | 12.1 | 19.2 | 12.2 | 9.4 |

Example 2

A variety of electrodes require the silver component to be 'pre-chlorinated' in order to work with different gels. This requirement means that the purely silver coated particles must first be converted to an Ag/AgCl coating. Silver-coated glass particles were added to a 0.2 wt % solution of $NaClO_2$ dissolved in water. The particles were stirred in the solution, and then filtered and washed with water before being dried.

Fibers were used to determine the mixing ratio of AgCl particles to Ag particles. Commercially available inks use an AgCl:Ag mix ratio of between 50:50 and 20:80 for best results. Electrodes were made using sensors coated with silver particles at different ratios of silver particles to chlorinated silver particles to determine if there is such an optimal level with the present coating method. Table 2 summarizes the electrical performance of electrodes assembled with Ag/AgCl fiber mixtures on sensors. Testing was performed as per AAMI EC12:2000 method TS-667. Desired performance limits are: DC Offset (DCO)=100 mV, Simulated Defibrillation Recovery (SDR)=100 mV. The results in Table 2 show that a mixture between 50 and 75% AgCl fibers gives the best results for defibrillation recovery.

TABLE 2

| AgCl:Ag fibers | DCO (mV) | SDR (mV) |
| --- | --- | --- |
| 100:0 | 1.4 | 7.8 |
| 75:25 | 1.2 | 6.5 |
| 50:50 | 0.7 | 6.8 |
| 25:75 | 0.4 | 7.9 |

Electrodes were made in the same fashion as Example 1 using silver-coated glass particles with a 50:50 Ag:AgCl fiber ratio embedded in the conductive resin. The electrodes were compared to commercially available Ag/AgCl electrodes (S-9129/300/SP/0.065/AGCL, from Select Engineering, Fitchburg, Mass.). Table 3 summarizes the electrical performance of electrodes assembled with Ag/AgCl-coated particles on sensors. Testing was performed as per AAMI EC12:2000 method TS-667. Desired performance limits are: DC Offset (DCO)=100 mV, AC Impedance (ACZ)=3000 Ohm, Simulated Defibrillation Recovery (SDR)=100 mV.

TABLE 3

| Sample | Ag Fibers | Ag Beads | Ag Flakes | Reference |
| --- | --- | --- | --- | --- |
| Silver Type | 20 wt % Ag/AgCl coated glass | 12 wt % Ag/AgCl coated glass | 30 wt % Ag/AgCl coated glass | Electroplated part |
| Sensor | 40% C fiber in resin | 40% C fiber in resin | 40% C fiber in resin | 20% C fiber in resin |
| DCO (mV) | 0.5 | 0.7 | 0.8 | 0.5 |
| ACZ (Ohm) | 193 | 273 | 211 | 110 |
| SDR (mV) | 6.2 | 6.7 | 6.3 | 8.7 |

Example 3

Figure 2A:
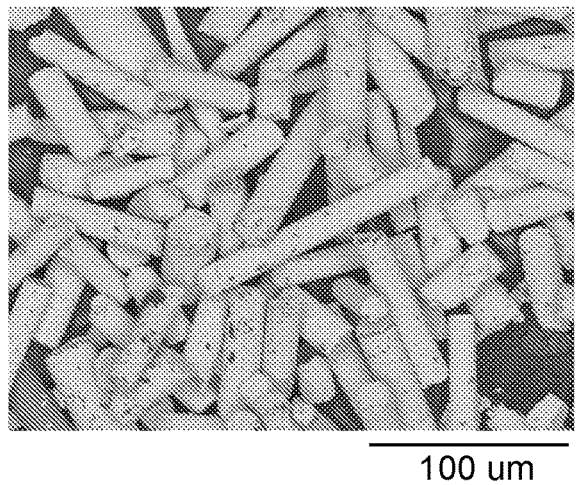
FIG. 2A is a scanning electron micrograph (SEM) image at 600× magnification of the top face of LDPE film showing silver-coated glass fibers thermally embedded, therein.
Figure 2B:
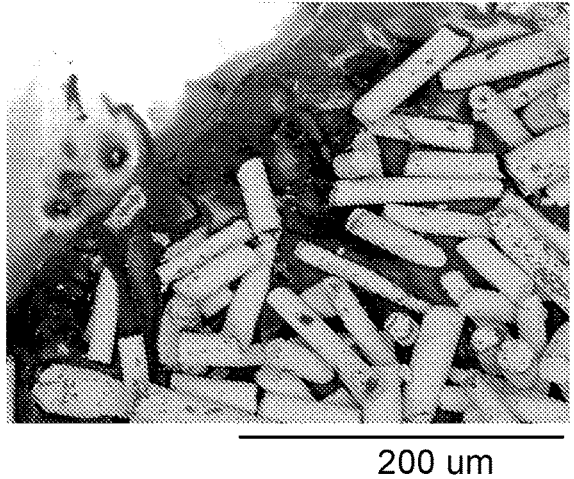
FIG. 2B is a scanning electron micrograph (SEM) image at 500× magnification, showing silver-coated glass fibers near the edge of the LDPE film in which they are thermally embedded.
Figure 2C:
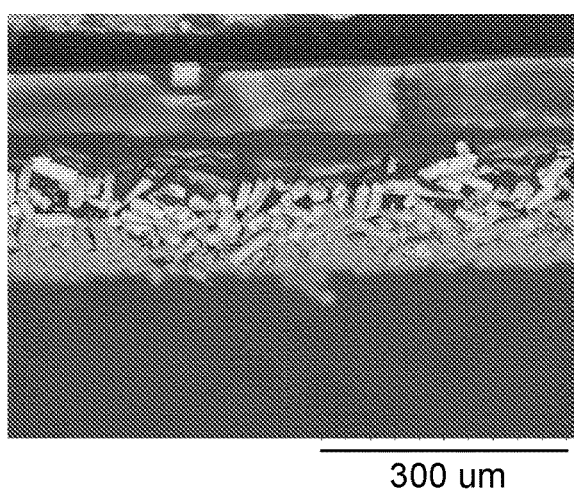
FIG. 2C is a scanning electron micrograph (SEM) image at 250× magnification, of a cross section showing silver-coated glass fibers thermally embedded in a surface of a 127 micrometer thick LDPE film with enough density for percolation.
Figure 2D:
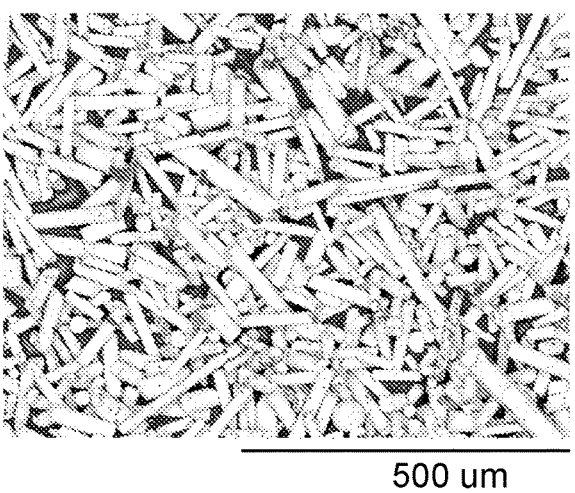
FIG. 2D is a scanning electron micrograph (SEM) image at 200× magnification, showing silver-coated glass fibers thermally embedded in a surface of a 127 micrometer thick LDPE film with enough density for percolation.

Ag/AgCl fiber mix described in Example 2 was used in another electrode construction. The fibers were used for a tab or resting style electrode. The fibers were embedded into a 5 mil low density polyethylene (LDPE) film using heated calender rolls such that the fiber density was sufficient for percolation. SEM micrographs of the embedded fibers are shown in FIG. 2. A 25.4 mm by 25.4 mm square with a tab was punched out using a die. An ionically conductive adhesive (R40D, available from 3M Company, St Paul, Minn.) was used instead of a conductive gel. A reference of 3M Red Dot™ resting electrode (2330, available from 3M Company, St Paul, Minn.) with the same conductive adhesive was used for comparison of performance. Table 4 summarizes the electrical performance of tab electrodes assembled with 50/50 Ag/AgCl fiber on LDPE film. Testing was performed as per AAMI EC12:2000 method TS-667. Desired performance limits are: DC Offset (DCO)=100 mV, AC Impedance (ACZ)=3000 Ohm, Simulated Defibrillation Recovery (SDR)=100 mV.

The present invention enables the use of cheap polymer substrates such as LDPE, compared to expensive primed and print-ready PET films. Additionally, for a similar coating weight, the silver-coated glass fibers embedded in a LDPE film may have lower impedance than the printed PET film due to a higher surface area of the embedded fiber layer. The embedded fiber layer will be thicker and have significantly rougher topography than a flexographically printed silver layer which would be very smooth.

TABLE 4

| Sample | Ag Fibers | Reference |
| --- | --- | --- |
| Silver Type | 20 wt % silver coated glass. 50% chlorinated. | Flexographic coated Ag/AgCl ink |
| Substrate | 5 mil LDPE (low density polyethylene) | 5 mil PET (polyethylene terephthalate) |
| DCO (mV) | 0.8 | 0.4 |
| ACZ (Ohm) | 80 | 440 |
| SDR (mV) | 17.6 | 20 |

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. An electrode sensor comprising:
a solid conductive polymeric substrate comprising electrically conductive polymers and/or an electrically conductive filler and having a contact surface; and,
a plurality of silver-coated particles thermally embedded into the contact surface of the solid conductive polymeric substrate,
wherein a portion of each of the plurality of silver-coated particles are sufficiently anchored into the contact surface and surrounded by the solid conductive polymeric substrate while another portion of each of the plurality of silver-coated particles is exposed such that the plurality of silver-coated particles are not dispersed throughout the bulk of the solid conductive polymeric substrate.

2. The electrode sensor according to claim 1, wherein the plurality of silver-coated particles have an average size in a range of 1-300 um.

3. The electrode sensor according to claim 1, wherein an amount of silver of the plurality of silver-coated particles distributed on the contact surface is 10 mg Ag/sq. in. or less.

4. The electrode sensor according to claim 1, wherein an amount of silver of the plurality of silver-coated particles distributed on the surface is 8 mg Ag/sq. in. or less.

5. The electrode sensor according to claim 1, wherein an amount of silver of the plurality of silver-coated particles distributed on the surface is an amount in a range of 1-6 mg Ag/sq. in.

6. The electrode sensor according to claim 2, wherein an amount of silver of the plurality of silver-coated particles provides the electrode sensor with a pre-determined recovery time from charge accumulated by the electrode sensor in a defibrillation event during heart fail.

7. The electrode sensor according to claim 1, wherein surface roughness as measured by the arithmetic average of the absolute values (Ra) is in a range of 1-15 micron.

8. The electrode sensor according to claim 1, wherein the particles comprise glass.

9. The electrode sensor according to claim 1, wherein the particles are fibers.

10. The electrode sensor according to claim 1 wherein the plurality of silver-coated particles are distributed non-continuously on the contact surface providing a plurality of conductive channels rather than a single conductive channel as provided by the continuous layer of silver resulting from ink printing or electroplating processes.

11. An electrode assembly comprising:
the electrode sensor as defined in claim 1;
a conductive stud for attaching a backing to the electrode sensor;
a conductive gel on a surface of the electrode sensor; and
a removable cover attached to the conductive gel.

12. The electrode assembly according to claim 11 which is an electrocardiogram electrode.

13. The electrode assembly according to claim 11 which is a resting electrode.

14. The electrode assembly according to claim 11 which is a monitoring electrode.

15. A process for producing the electrode sensor of claim 1 comprising: distributing the plurality of silver-coated particles only on the contact surface of the solid conductive polymeric substrate comprising the electrically conductive polymers and/or the electrically conductive filler, and thermally embedding the plurality silver-coated particles into the contact surface.

16. The process according to claim 15, wherein the plurality of silver-coated particles comprise glass.

17. The process according to claim 15, wherein the plurality of silver-coated particles have an average size in a range of 1-300 μm.

18. The process according to claim 15, wherein the plurality of silver-coated particles are distributed on the contact surface to provide an amount of 10 mg Ag/sq. in. or less on the contact surface.

19. The process according to claim 15, wherein the plurality of silver-coated particles are distributed on the contact surface to provide an amount of 8 mg Ag/sq. in. or less on the contact surface.

20. The process according to claim 15, wherein the thermal embedding comprises calendering or compression pressing.

* * * * *